United States Patent [19]

Shen

[11] Patent Number: 4,666,636
[45] Date of Patent: May 19, 1987

[54] PRODUCTION OF SODIUM PHENOL SULFONATE

[75] Inventor: Chung Y. Shen, St. Louis, Mo.

[73] Assignee: Monsanto Company, St. Louis, Mo.

[21] Appl. No.: 791,659

[22] Filed: Oct. 28, 1985

[51] Int. Cl.$^4$ .......................................... C07C 143/42
[52] U.S. Cl. ................................................ 260/512 R
[58] Field of Search .................................... 260/512 R

[56] References Cited

U.S. PATENT DOCUMENTS

| | | | |
|---|---|---|---|
| 2,166,136 | 7/1939 | Flett | 260/624 |
| 2,205,947 | 6/1940 | Flett | 260/512 |
| 2,223,363 | 12/1940 | Flett | 260/512 |
| 2,673,208 | 3/1954 | Andrews et al. | 260/400 |
| 3,772,379 | 11/1973 | Woodgate | 260/512 R |

*Primary Examiner*—Alan Siegel
*Attorney, Agent, or Firm*—R. Loyer

[57] ABSTRACT

A process for preparing anhydrous sodium phenol sulfonate low in APHA color wherein the hydrated material is subjected to a temperature in the range of from about 140° C. to 200° C. in an inert atmosphere for a period of time not exceeding two hours.

12 Claims, No Drawings

PRODUCTION OF SODIUM PHENOL SULFONATE

BACKGROUND OF THE INVENTION

This invention relates to the production of sodium phenol sulfonate. More particularly it relates to a process for preparing substantially anhydrous sodium phenol sulfonate.

Sodium phenol sulfonate is a valuable intermediate employed in the manufacture of alkanoyloxybenzene sulfonates. Sodium alkanoloxybenzene sulfonates are disclosed as being useful in a toilet bar in U.S. Pat. No. 3,503,888 issued Mar. 31, 1970 to R. O. Miller, et al. The preparation of sodium alkanoyloxybenzene sulfonates are generally performed by the reaction of an alkanoyloxychloride with sodium phenol sulfonate. One method of preparation wherein the above-mentioned reactants are brought together in the presence of an organic solvent such as dimethyl formamide is taught by F. Puschel and O. Todorov, Tenside 7 (1970) 249-54, 252. Another method for preparing alkanoyloxybenzene sulfonates is disclosed in EPO publication 148,148 wherein substantially solid anhydrous sodium phenol sulfonate is reacted with an alkanoyloxyhalide at a temperature in the range of about 90° C. to about 200° C. in the substantial absence of a solvent or inert reaction medium.

Alkanoyloxybenzene sulfonates, and particularly the sodium derivative, are utilized in detergent materials wherein the color of the material is important to commercial utility. It is preferred that the material be colorless or to have as little color as possible such as 50 APHA or below based upon a 10% dry weight solution. However, in the preparation of sodium phenol sulfonates to provide substantially anhydrous material, it has been found unexpectedly that drying the commonly available dihydrate crystals does not occur below about two percent water level without excessive heating resulting in discoloration of the product and some degradation which forms undesirable by-products.

There is needed an efficient and facile process for the manufacture of substantially anhydrous sodium phenol sulfonate having acceptable color for detergent utility.

SUMMARY OF THE INVENTION

In accordance with this invention there is provided a process for producing anhydrous sodium phenol sulfonate comprising subjecting the sodium phenol sulfonate hydrate to a temperature in the range of above about 140° C. but below about 220° C. under an inert atmosphere for a period of time sufficient to remove water of hydration. Preferably the process of this invention is operated at a temperature in the range of from about 170° C. to about 200° C. It has been found that substantially anhydrous product of acceptable color and free from by-products is obtained provided the sodium phenol sulfonate is exposed to the dehydration process for a period of time less than two hours. The exposure of sodium phenol sulfonate to elevated temperatures required to remove the water hydration for an extended period of time such as for more than two hours results in discolored material often with by-product formation and not generally acceptable for detergent utility.

Typically, an inert atmosphere is provided over the sodium phenol sulfonate by any conventional means such as by providing high vacuum or by flushing the container with an unreactive or inert gas such as nitrogen. Other gases which would provide an unreactive atmosphere are, for example carbon dioxide, argon, and the like. A suitable inert gas is a stable material that does not react with sodium phenol sulfonate. The inert atmosphere can contain a low level of oxygen such as less than about 5%, by weight. The presence of greater than about 5%, by weight oxygen in the atmosphere results in deterioration of sodium phenol sulfonate under drying conditions which are preferred, i.e., 140° C.–220° C.

DETAILED DESCRIPTION OF THE INVENTION

Sodium phenol sulfonate, as noted above, is normally provided as the dihydrate. Attempts to dehydrate this material in air at an elevated temperature such as about 200° C. results in discoloration, generation of phenol and byproduct formation. Further, anhydrous sodium phenol sulfonate will decompose to yield water and by-product when exposed to temperatures at or above 200° C. in air. Attempts to dehydrate the material at lower temperatures has resulted in inefficient and incomplete dehydration.

It has been discovered that the dihydrate can be dried to a water level approximately equal to the ¼ hydrate composition relatively easy but reduction of water content in the hydrated material below the ratio of about 4 moles of sodium phenol sulfonate to 1 mole of water is not feasible at low temperatures in an air atmosphere without formation of color, by-product, or both.

The term "anhydrous sodium phenol sulfonate" as employed herein means the substantial absence of water. However, small amounts of water up to about 0.1 percent by weight are tolerable and it is understood that sodium phenol sulfonate having such small amounts are within the term "anhydrous" as employed herein. Although there are ortho, meta and para isomers of sodium phenol sulfonate, only the para isomer is of interest here because the para isomer can be easily recovered from a neutralized solution of phenol sulfonic acid as the dihydrate intermediate of high purity. Therefore the term "sodium phenol sulfonate" means that para isomer having less than about 1%, by weight, of other isomers. It should also be noted that an inert material such as sodium sulfate, sodium carbonate, sodium phosphate and the like may be present in the sodium para phenol sulfonate. It is preferred that at least 50% of the material is sodium para phenol sulfonate.

Any number of dehydration vessels can be employed in the process of this invention. However, it has been found that a stirred bed chamber such as occurs in a fluid bed, a rotary dryer or an indirectly heated, agitated vessel is preferred whereby nitrogen atmosphere can be employed to sweep away the water vapor released from the sodium phenol sulfonate. The bed depth can be any amount of thickness such as about ¼ inch in a stationary bed. Thicker bed depth can be employed but a stirring mechanism for the thicker bed is required. Heating by means of internal baffles or pipes is also preferred over external heating of the vessel whereby the sodium phenol sulfonate is raised to a temperature within the range specified above.

The practice of the present invention will now be illustrated and detailed by various specific examples giving preferred embodiments of the invention. These examples are not intended, however, to limit the spirit and scope of the disclosure other than as stated here.

EXAMPLE I

Sodium paraphenol sulfonate dihydrate was produced from a neutralized phenol sulfonic acid solution. The dihydrate crystals were obtained by filtration and washed with distilled water. The crystals as analyzed by high pressure liquid chromatography procedure contained 99.7% para- and 0.3% ortho- moities.

The wet crystals were first dried at 120° C. in an evaporating dish in an oven. The product dried to 2.0–2.8% water when the product temperature reached 120° C. The water level did not show any change over a prolonged time. The dried intermediate had an apparent composition of sodium paraphenol sulfonate quarter hydrate with little color formation.

EXAMPLE II (Prior Art)

Sodium paraphenol sulfonate with about 2.5% water was dried in an oven at 200° C. to remove the last amount of water. In less than two hours, the product surface turned to a brownish color. Using carbon-13 NMR analysis, it was found that the following by-products were produced

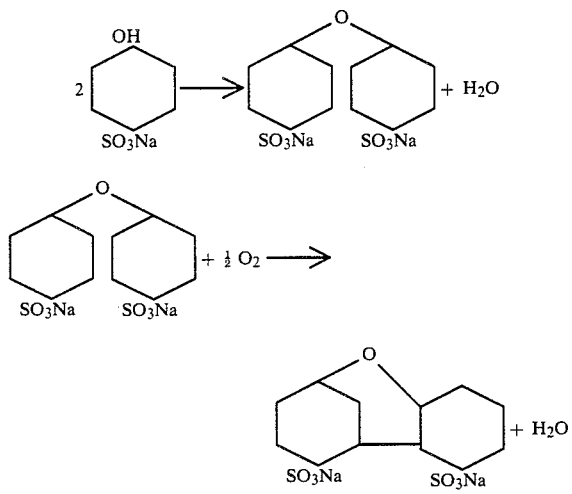

The by-product coated sodium paraphenol sulfonate had a very poor reactivity with fatty acid chloride.

EXAMPLE III

A 100 g sample of 100 micron average size dried sodium paraphenol sulfonate quarter hydrate with a water content of 2.8% was placed in an agitated one liter Ace reactor, indirectly heated by an oil bath. The sulfonate bed temperatures were controlled by adjusting the oil bath temperature. Dry nitrogen with varying amounts of oxygen or ambient air was passed through the bed at one liter per minute rate. After two hours, the remaining water level in a portion of the sample and the color of a 10% solid aqueous solution were analyzed. The procedures were repeated many times except that nitrogen with different amounts of oxygen or ambient air was employed. The results are summarized in the table below.

|   | Gas Composition % Oxygen in $N_2$ | Bed Temp °C. | Residual Water % | 10% Solution Color APHA |
|---|---|---|---|---|
| (a) | 0 | 160 | 1.2 | 10 |
| (b) | 0 | 180 | 0.06 | 20 |
| (c) | 0 | 200 | 0.05 | 35 |
| (d) | 0 | 240 | 0.04 | 40 |
| (e) | 0 | 260 | 0.04 | 200 |
| (f) | 2.2 | 160 | 1.2 | 35 |
| (g) | 2.2 | 180 | 0.06 | 40 |
| (h) | 5.3 | 160 | 1.2 | 35 |
| (i) | 5.3 | 180 | 0.06 | 100 |
| (j) | Air | 140 | 2.0 | 40 |
| (k) | Air | 160 | 1.3 | 150 |

Dried sodium paraphenol sulfonate with an APHA color of less than about 50 and a water level of less than 0.1 percent will react with nonanoyl chloride to give the desired color of less than 100 APHA and assay of greater than 95% as sodium nonanoyl oxybenzene sulfonate.

EXAMPLE IV

To a vertical column fluidized bed dryer having a ¼" thick stationary bed there is charged crystalline parasodium phenol sulfate containing 2.8% water of hydration. The fluidization velocity of the bed was 0.23 ft./second at a bed density of 31 lb./ft³. The bed temperature was maintained at 180° C. The feed material contained dry nitrogen at the rate of 2.85 lb./lb. of dry parasodium phenol sulfonate and the mixture passed through the dryer so as to provide a retention time of 30 minutes. The dried parasodium phenol sulfonate was found to contain 0.1% by weight water and did not change color materially.

EXAMPLE V

The same equipment and test material used in Example III are used. Instead of passing a gas stream to control the atmosphere of the drying bed, vacuum is applied with a vacuum pump and a control valve to adjust the level of vacuum. The remaining water level and color of the 10% solutions are analyzed at various time intervals. The results are summarized below.

|   | Total Pressure Above The Drying Bed, Torr | Time Duration Hr | Bed Temp °C. | Residual Water % | 10% Solution Color APHA |
|---|---|---|---|---|---|
| (a) | 10 | 0.1 | 180 | 0.08 | 10 |
|   |   | 0.5 | 180 | 0.05 | 15 |
| (b) | 25 | 0.1 | 180 | 0.15 | 10 |
|   |   | 0.5 | 180 | 0.08 | 15 |
| (c) | 50 | 0.1 | 180 | 0.20 | 10 |
|   |   | 0.5 | 180 | 0.10 | 15 |
| (d) | 100 | 0.5 | 180 | 0.60 | 15 |
|   |   | 1.0 | 180 | 0.40 | 20 |
|   |   | 2.0 | 180 | 0.10 | 35 |
| (e) | 10 | 0.1 | 200 | 0.04 | 15 |
| (f) | 10 | 0.1 | 220 | 0.04 | 50 |
| (g) | 10 | 0.1 | 240 | 0.04 | 200 |

The product exposed at 240° C. in high vacuum showed signs of decomposition.

EXAMPLE VI (Prior Art)

100 g sodium paraphenyl sulfonate dihydrate with a moisture content of 14.61 percent was placed in an evaporating dish and heated to 120° C. in a vacuum oven. With an efficient vacuum pump, the vacuum oven pressure was lowered to 8 mm Hg absolute. After 20 hours, the sample was analyzed to have 2.29% water by weight.

Although the invention has been described in terms of specified embodiments which are set forth in considerable detail, it should be understood that this is by way of illustration only and that the invention is not necessarily limited thereto since alternative embodiments in operating techniques will become apparent to those skilled in the art in view of the present disclosure. Accordingly, modifications are contemplated which can be made without departing from the spirit of the described invention.

I claim:

1. A process for producing substantially anhydrous sodium phenol sulfonate comprising subjecting sodium phenol sulfonate hydrate to a temperature in the range of above about 140° C. but below about 220° C. under an inert atmosphere for a period of time sufficient to substantially remove water of hydration.

2. The process of claim 1 wherein the period of time is less than 2 hours.

3. The process of claim 1 wherein the temperature is in the range of from about 170° C. to about 200° C.

4. The process of claim 1 wherein the inert atmosphere comprises nitrogen.

5. The process of claim 1 wherein the inert atmosphere is a vacuum.

6. The process of claim 1 wherein the period of time is in the range of about 30 minutes.

7. The process of claim 1 wherein the sodium phenol sulfonate is heated in a fluid bed dryer.

8. The process of claim 7 wherein the bed temperature is about 180° C.

9. The process of claim 8 wherein the inert atmosphere comprises nitrogen.

10. The process of claim 7 wherein the bed density is in the range of from about 30 to 35 pounds per cubic foot.

11. The process of claim 9 wherein the sodium phenol sulfonate is comprised of at least 50%, by weight, sodium para phenol sulfonate and the remainder is inert material.

12. The process of claim 11 wherein the color of the dried anhydrous sodium para phenol is below about 50 APHA.

* * * * *

UNITED STATES PATENT AND TRADEMARK OFFICE
CERTIFICATE OF CORRECTION

PATENT NO. : 4,666,636
DATED      : May 19, 1987
INVENTOR(S) : C. Y. Shen

It is certified that error appears in the above-identified patent and that said Letters Patent are hereby corrected as shown below:

In column 3, lines 40 - 45, delete present structure and insert therefor

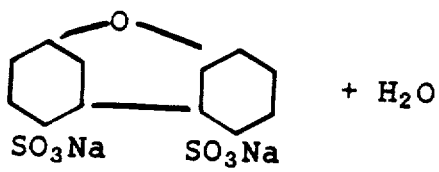 + $H_2O$

Signed and Sealed this

First Day of December, 1987

*Attest:*

DONALD J. QUIGG

*Attesting Officer*   *Commissioner of Patents and Trademarks*